(12) United States Patent
Ferek-Petric

(10) Patent No.: US 6,480,744 B2
(45) Date of Patent: Nov. 12, 2002

(54) IMPLANTABLE MEDICAL DEVICE TELEMETRY CONTROL SYSTEMS AND METHODS OF USE

(75) Inventor: Bozidar Ferek-Petric, Zagreb (HR)

(73) Assignee: Medtronic, Inc., Minneapolis, MN (US)

( * ) Notice: Subject to any disclaimer, the term of this patent is extended or adjusted under 35 U.S.C. 154(b) by 99 days.

(21) Appl. No.: 09/727,462

(22) Filed: Dec. 4, 2000

(65) Prior Publication Data

US 2002/0099424 A1 Jul. 25, 2002

(51) Int. Cl.[7] .............................. A61N 1/37; B60K 28/06
(52) U.S. Cl. ........................... 607/60; 607/32; 128/903; 340/576; 180/272; 701/36; 701/70
(58) Field of Search .............................. 607/60, 30, 32, 607/52; 128/903, 904; 340/573.1, 576; 180/272; 701/36, 48, 70

(56) References Cited

U.S. PATENT DOCUMENTS

| | | | | |
|---|---|---|---|---|
| 4,295,474 A | * | 10/1981 | Fischell | .................. 128/697 |
| 5,562,713 A | * | 10/1996 | Silvian | .................. 607/60 X |
| 5,674,249 A | * | 10/1997 | De Coriolis et al. | ...... 607/60 X |
| 6,115,636 A | * | 9/2000 | Ryan | .......................... 607/60 |
| 6,230,084 B1 | * | 5/2001 | Kijima et al. | ............ 701/36 X |
| 6,272,379 B1 | * | 8/2001 | Fischell et al. | ................ 607/5 |

* cited by examiner

Primary Examiner—Kevin Lee
(74) Attorney, Agent, or Firm—Thomas F. Woods; Eric R. Waldkoetter; Tom G. Berry

(57) ABSTRACT

Implantable medical device telemetry control systems and methods are used to coordinate medical therapy delivery from an implantable medical device (IMD) to a patient-driver of a vehicle, e.g., automobile. In one embodiment, the control system alerts the patient-driver to stop the vehicle after a medical event is detected by the IMD. Once the vehicle is stopped, the therapy is delivered. In another embodiment, a vehicle control module is provided which actively controls various subsystems of the car in response to a detected medical event. For example, the vehicle control module may control vehicle engine speed or vehicle braking to slow or stop the vehicle or, alternatively, assist the patient-driver in stopping the vehicle, prior to or simultaneously with therapy delivery. In still other embodiments, an emergency communication is automatically transmitted to emergency personnel informing the same of the medical event.

71 Claims, 9 Drawing Sheets

IMPLANTABLE MEDICAL DEVICE TELEMETRY CONTROL SYSTEMS AND METHODS OF USE

FIELD OF THE INVENTION

The present invention relates to implantable medical devices such as cardiac pacemakers and defibrillators. More particularly, the present invention pertains to implantable medical device telemetry control systems and methods for their integration and use with automotive vehicles.

BACKGROUND

A wide variety of implantable medical devices (IMDs) are known and commercially available. Generally, these devices utilize a bio-compatible case having a connector block mounted thereto. The connector block includes receptacles for leads that may be used for electrical stimulation and/or for sensing physiological activity. For example, an implantable cardiac device, e.g., an implantable pacemaker-cardioverter-defibrillator (PCD), may use such leads to monitor activity of a human heart and to deliver therapy thereto in the event undesirable heart activity is detected. For the sake of brevity, the remainder of this discussion will focus on IMDs for treatment of cardiac conditions. However, it is understood that the present invention is equally applicable to IMDs of most any purpose.

For many cardiac IMD patients, all that is required to maintain regular cardiac function is pacing shocks delivered to a particular area of the heart. These cardiac events and the resulting pacing shocks are generally mild and the patient typically experiences no significant sensation. However, for more serious cardiac conditions, e.g., ventricular fibrillation (VF) and ventricular tachycardia (VT), the patient may experience immediate incapacitation and even loss of consciousness. Further, the therapy delivered in response to such severe cardiac events is often sufficient to cause significant discomfort, further disorienting or incapacitating the patient. Accordingly, IMD patients who suffer from more severe cardiac conditions are often restricted from driving a vehicle or from operating other potentially dangerous machinery as the occurrence of a severe cardiac event may endanger their lives and/or the lives of others.

Yet for many cardiac IMD patients, the occurrence and severity of cardiac arrhythmias does not warrant absolute driving restrictions. For example, some PCD patients may never experience a cardiac event at all, let alone during the limited time they may be driving. In fact, at least one study has shown that recipients of implantable cardioverter defibrillators have no more frequent motor vehicle accidents than the general population. See "Modification of Patient Driving Behavior After Implantation of a Cardioverter Defibrillator," Conti et al., PACE, Vol. 20, September 1997, pp 2200–2204, 2203. Nonetheless, given even the potential for harm to the patient-driver, passengers, pedestrians, and surrounding vehicles, it is often perceived that driving restrictions for some or all cardiac IMD patients are justified.

The ability to drive, however, is viewed as an important aspect of maintaining one's independence. Accordingly, a solution short of totally restricting the IMD patient's driving privileges would be advantageous.

One partial solution is discussed in U.S. Pat. No. 5,332,400 to Alferness, entitled "Atrial Defibrillator and Method for Providing Pre-Cardioversion Warning," issued Jul. 26, 1994. The '400 patent describes an implantable atrial defibrillator capable of providing warning electrical energy to the patient when the patient's heart is in need of cardioversion before the delivery of cardioverting electrical energy. The warning electrical energy is of a quantity that is less discomforting than the quantity required to cardiovert the atria. An implantable sensor having a similar warning device is described in U.S. Pat. No. 5,404,877 to Nolan et al., entitled "Leadless Implantable Sensor Assembly and a Cardiac Emergency Warning Alarm," issued Apr. 11, 1995.

While effective, the warning devices described in the '400 and '877 patents rely on the judgement of the driver to take immediate precautionary measures, e.g., stop. Further, for patients who suffer a severe cardiac event, e.g., a hemodynamically unstable VT or VF, therapy must typically be delivered immediately. In such situations, the time delay between warning and therapy delivery is not always sufficient to permit the driver to take adequate precautionary measures.

While they do not warn the patient of impending therapy, other devices are known which can monitor implant status and locate the patient based on global positioning system (GPS) coordinates. For instance, see U.S. Pat. No. 5,752,976 to Duffin et al., entitled "World Wide Patient Locator and Data Telemetry System for Implantable Medical Devices," issued May 19, 1998. The '976 patent describes a system for communicating patient device information to and from a medical device implanted in an ambulatory patient and a remote medical support network.

U.S. Pat. No. 5,729,205 to Kwon, entitled "Automatic Transmission System of an Emergency Signal and a Method thereof Using a Driver's Brain Wave," issued Mar. 17, 1998, describes a system which enables police and hospitals to provide a proper and immediate rescue operation for those involved in an accident. The system operates by transmitting an emergency signal via GPS. The signal is derived from a particular brain wave generated when the driver is in critical condition.

Accordingly, various implementations of systems for warning a patient of impending cardiac therapy are known as are systems for transmitting IMD status or patient status/location to remote facilities. These systems are described above and in the documents listed in Table I below.

TABLE 1

| Pat. No. | Inventor | Issue Date |
| --- | --- | --- |
| 5,332,400 | Alferness | July 26, 1994 |
| 5,404,877 | Nolan et al. | April 11, 1995 |
| 5,752,976 | Duffin et al. | May 19, 1998 |
| 5,729,205 | Kwon | March 17, 1998 |

All documents listed in Table 1 herein above are hereby incorporated by reference in their respective entireties. As those of ordinary skill in the art will appreciate readily upon reading the Summary of the Invention, Detailed Description of the Embodiments, and claims set forth below, many of the devices and methods disclosed in the documents of Table 1 and others documents incorporated by reference herein may be modified advantageously by using the teachings of the present invention.

SUMMARY OF THE INVENTION

The present invention has certain objects. That is, various embodiments of the present invention provide solutions to one or more existing problems with respect to vehicle operation by IMD patients. One such problem involves the need to warn the patient-driver of a detected medical event and the onset of IMD therapy. In many instances, adequate warning permits the patient-driver to direct the vehicle to a safe and stopped position prior to therapy delivery. Another problem for patient-drivers with IMDs concerns more severe medical events, e.g., ventricular tachycardias, that can incapacitate the patient or even lead to loss of consciousness. If such an event occurs during driving, the patient-driver may lose consciousness before reaching a safe and stopped position. Other problems include the need to promptly notify emergency personnel of the medical event and the precise location of the patient-driver.

The IMD control systems and methods of the present invention provide one or more of the following advantages. The IMD is able to transmit an event signal indicative of the occurrence of a medical event, e.g., cardiac arrhythmia, to a vehicle control module associated with the vehicle. The vehicle control module may provide a warning alert to the patient-driver that a medical event has occurred and therapy is required. Where the nature of the medical event permits, the driver may be instructed to stop the vehicle as soon as possible.

Where the medical event is more serious, the vehicle control module may command the vehicle to slow or stop with little or even no input from the patient-driver. This is achieved via a command signal generated by the vehicle control module. In one embodiment, the command signal is transmitted to the vehicle ignition system, commanding the vehicle engine to slow or stop. In another embodiment, the command signal is provided to the brake system commanding the brake system to stop the vehicle. These command signals may be capable of completely stopping the vehicle without reliance on input from the patient-driver. Accordingly, telemetry control systems and methods according to the present invention are advantageous in that they permit assisted vehicle control in the event an IMD patient-driver experiences a medical event during vehicle operation.

The vehicle control system may also operate with a communication module such as a cellular telephone system. Upon the occurrence of a medical event, the vehicle control system may initiate an automated emergency call, alerting local emergency personnel to the medical event. A GPS module may, in conjunction with the communication module, provide the location of the vehicle, expediting arrival of emergency personnel. Other embodiments of the present invention may activate and/or control other vehicle subsystems. For instance, external emergency signals may be activated to notify other drivers.

Some embodiments of the present invention include one or more of the following features: an IMD capable of delivering a therapy to a patient-driver and further capable of transmitting an event signal; a telemetry communication module capable of receiving the event signal; a vehicle having an engine, a brake system, an ignition system, a warning system, a communication module and a GPS module; a vehicle control system operable to manipulate one or more vehicle subsystems and generate a status signal based thereon; and a device receiver associated with the IMD for receiving the status signal from the vehicle control system.

Other embodiments include one or more of the following features: providing an implantable medical device in a patient driver; monitoring a hemodynamic parameter such as blood pressure; providing a vehicle control module associated with a telemetry communication module; sensing a medical event with the implantable medical device; generating an event signal with the implantable medical device; transmitting the event signal to the telemetry control module; interrogating the status of the vehicle; manipulating the status of the vehicle; activating a warning indicator; commanding the ignition system to slow or stop the vehicle engine; commanding the brake system to slow or stop the vehicle; generating a status signal with the vehicle control module; transmitting the status signal from the telemetry control module to the implantable medical device; delivering therapy to the patient-driver with the implantable medical device; automatically notifying emergency personnel of the medical event; transmitting the vehicle location to emergency personnel; and activating external emergency signals on the vehicle.

The above summary of the invention is not intended to describe each embodiment or every implementation of the present invention. Rather, a more complete understanding of the invention will become apparent and appreciated by reference to the following detailed description and claims in view of the accompanying drawings.

BRIEF DESCRIPTION OF THE DRAWINGS

The present invention will be further described with reference to the drawings, wherein.

DETAILED DESCRIPTION OF THE EMBODIMENTS

Figure 1:
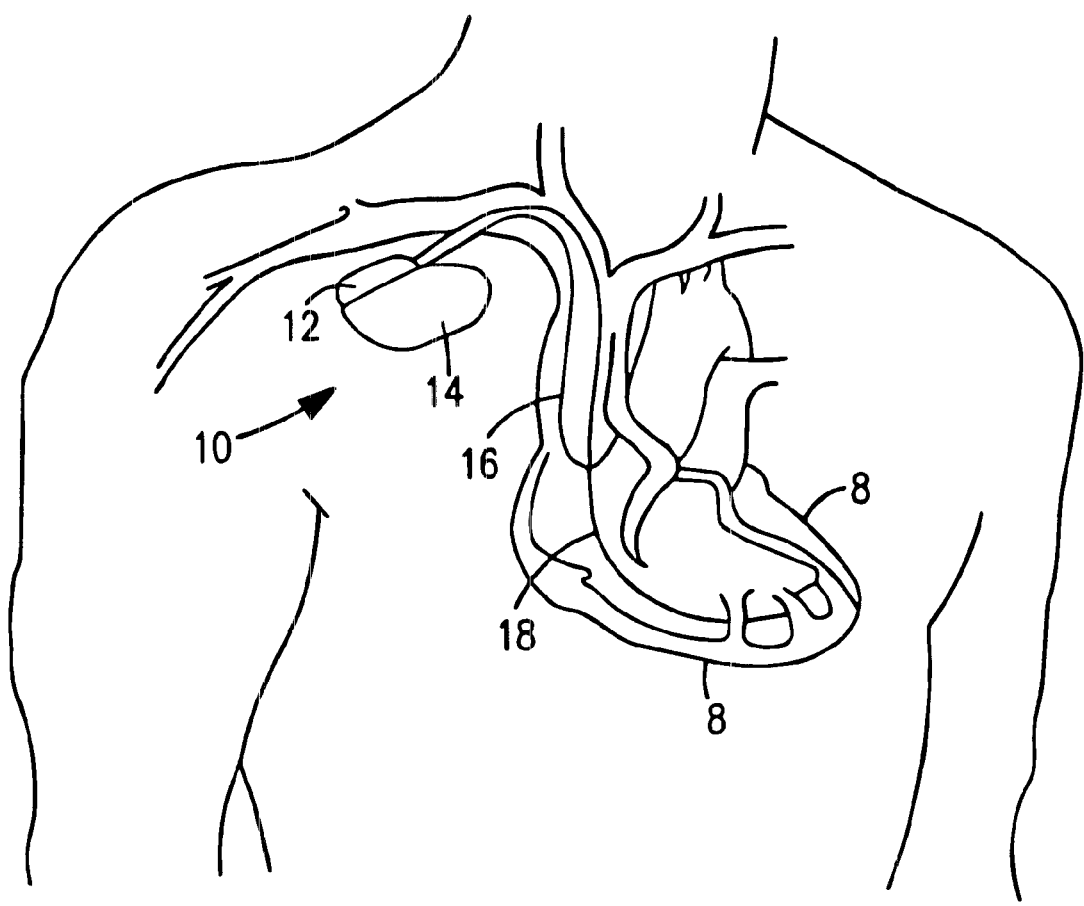
FIG. 1 is an implantable medical device (IMD) in accordance with one embodiment of the invention, wherein the IMD is implanted within a body of a patient.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18, sense electrical signals attendant to the depolarization and repolarization of the heart 8, and further provide pacing pulses for causing depolarization of cardiac tissue in the vicinity of the distal ends thereof. Leads 16 and 18 may have, for example, unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson.

Figure 2:
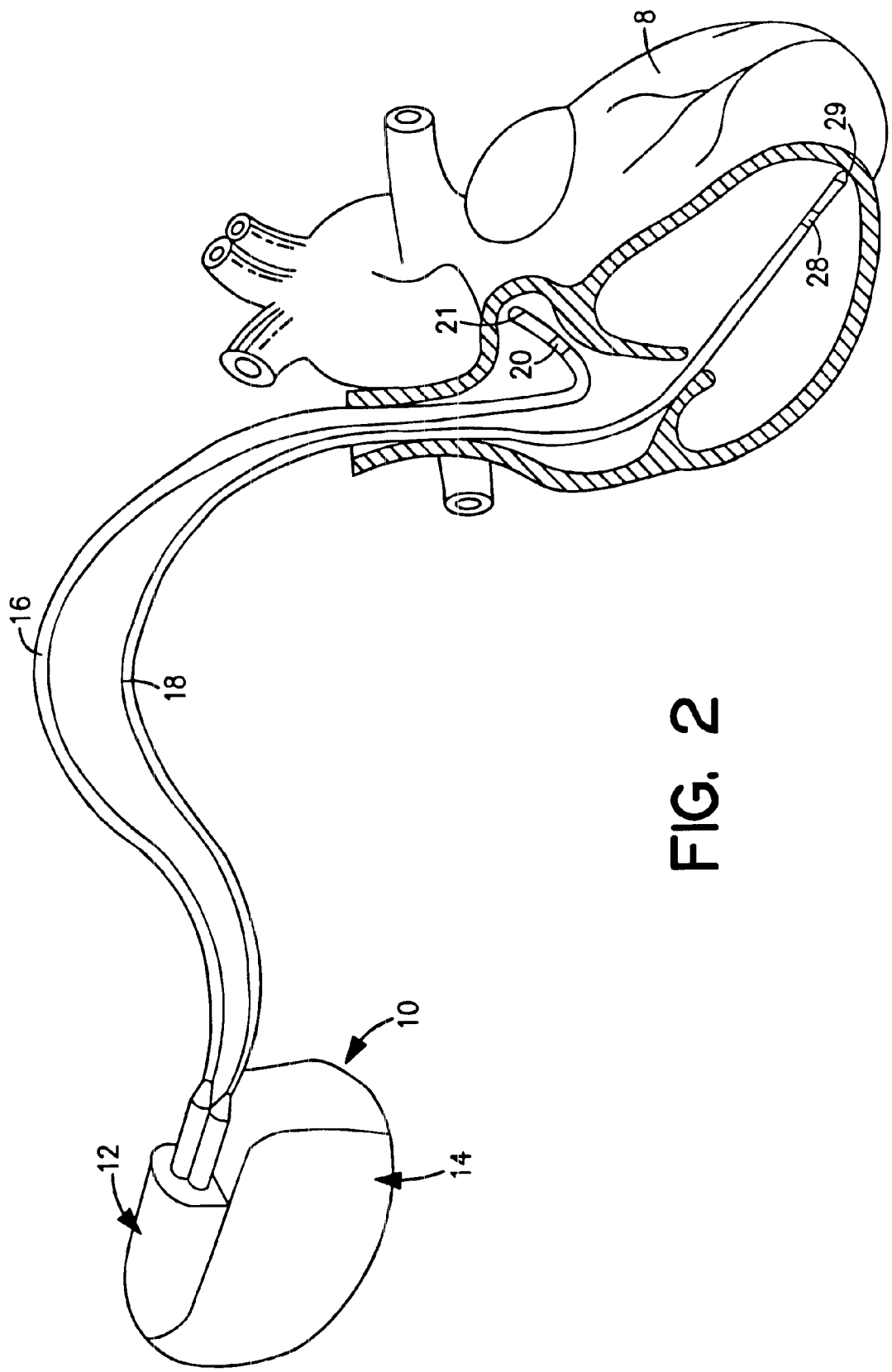
FIG. 2 is an enlarged view of the IMD of FIG. 1 diagrammatically illustrating coupling with the patient's heart in accordance with one embodiment of the invention.

FIG. 2 shows connector module 12 and hermetically sealed enclosure 14 of IMD 10 located near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
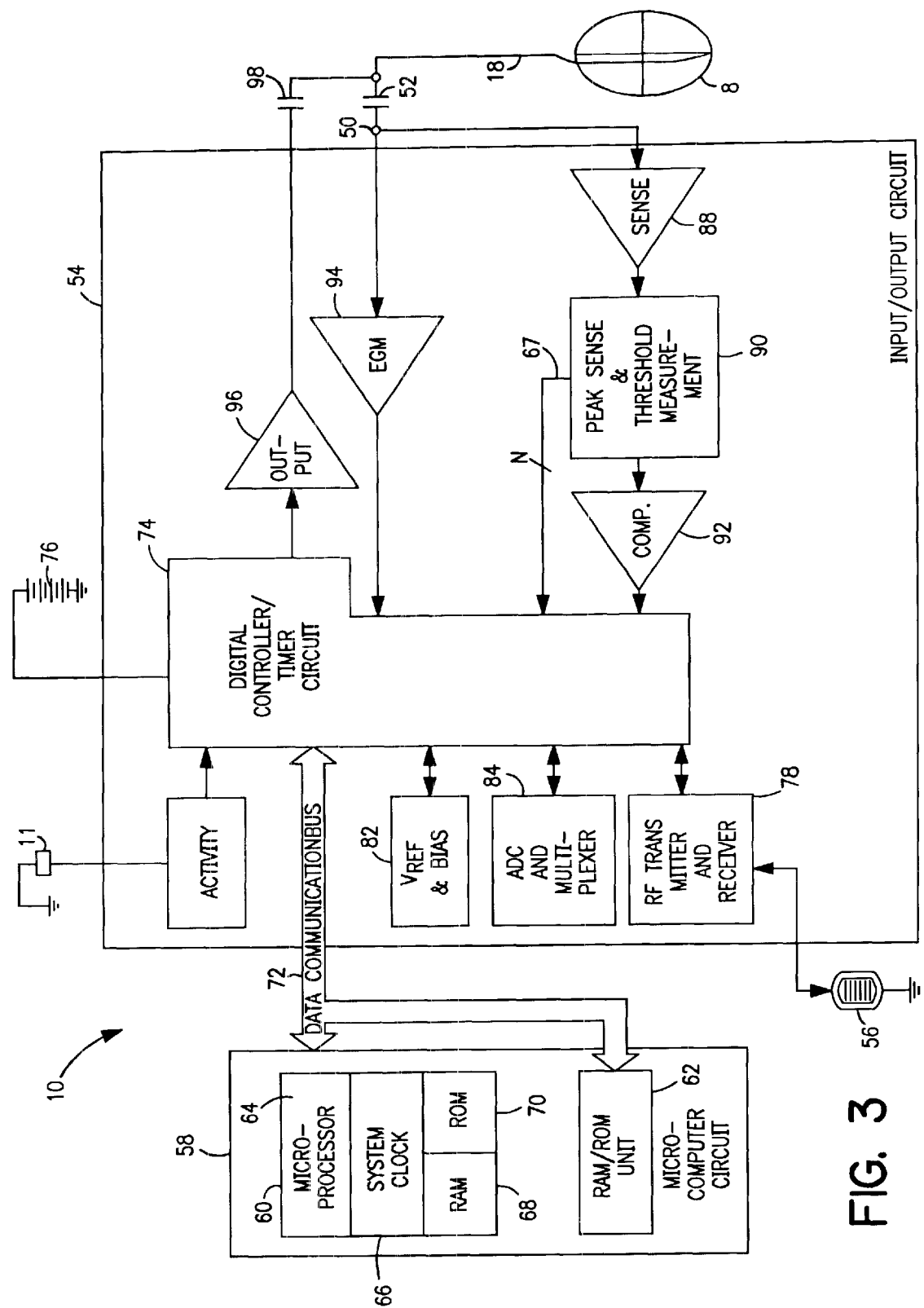
FIG. 3 is a functional block diagram of an IMD in accordance with one embodiment of the present invention.

FIG. 3 is a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,354,319 to Wyborny et al. The programming methodology disclosed in Wyborny et al.'s '319 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to inpuvoutput circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,556,063 issued to Thompson et al., or to that disclosed in the above-referenced '319 patent to Wybomy et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

$V_{REF}$ and Bias circuit 82 (see FIG. 3) most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified,signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al. Output pulse generator 96 provides pacing stimuli to patient's heart 8 through coupling capacitor 98, for example, in response to a pacing trigger signal provided by digital controller/timer circuit 74 each time the escape interval times out, in response to an externally transmitted pacing command or in response to other stored commands as is well known in the pacing art. By way of example, output amplifier 96 may correspond generally to an output amplifier disclosed in U.S. Pat. No. 4,476,868 to Thompson.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, WI, VOO and VVT modes. In other preferred embodiments of the present invention, IMD 10 may operate in various rate-responsive modes, including, but not limited to, DDDR, DDIR, WIR, VOOR and VVTR modes. Some embodiments of the present invention are capable of operating in both non-rate-responsive and rate responsive modes. Moreover, in various embodiments of the present invention, IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Further, the present invention is not limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single, dual-, triple- or quadruple- chamber pacemakers or other types of IMD's. See, for example, U.S. Pat. No. 5,800,465 to Thompson et al.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker, Jr. et al.

Figure 4:
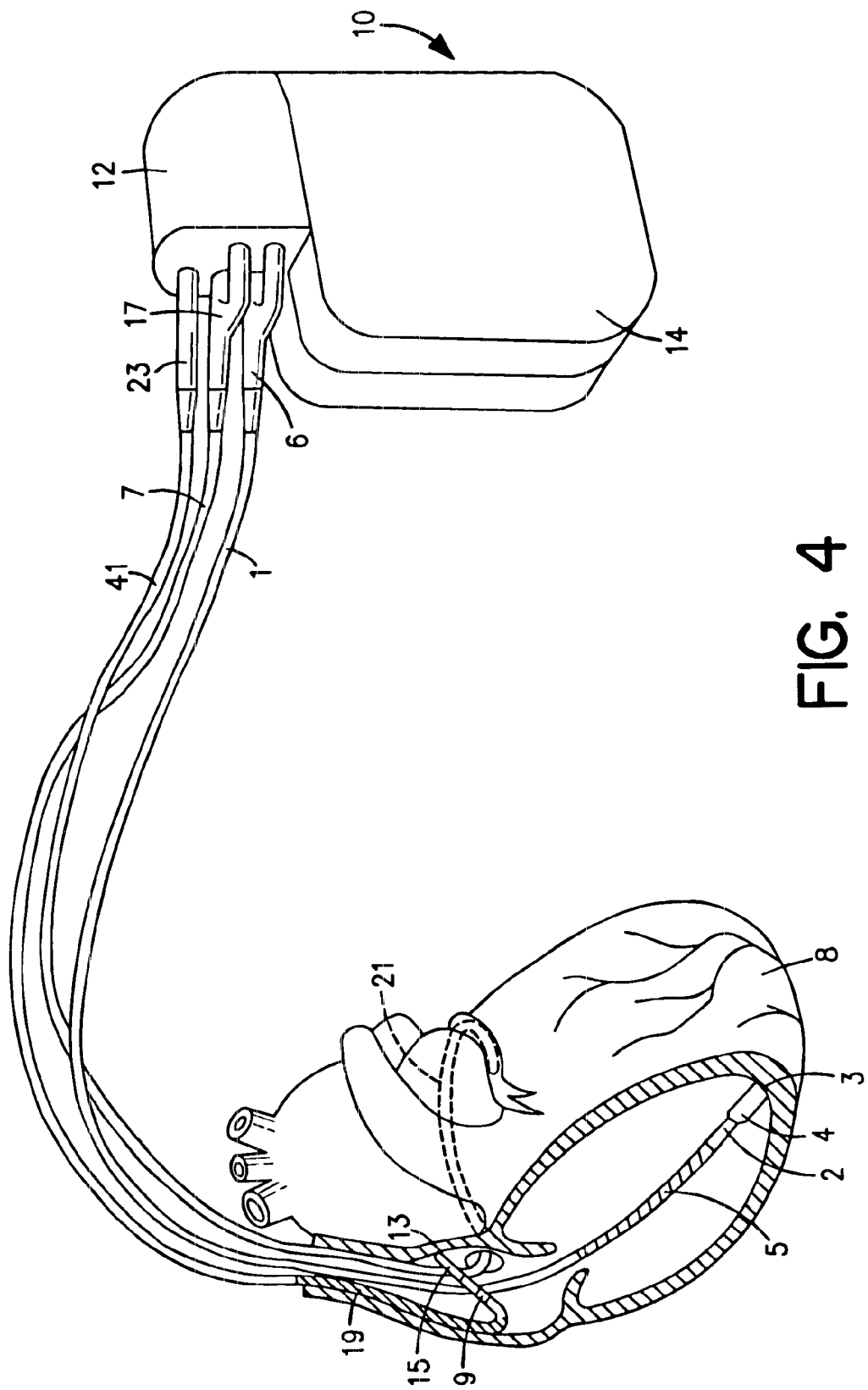
FIG. 4 is an IMD in accordance with another embodiment of the invention, wherein-the IMD is an implantable pacemaker-cardioverter-defibrillator (PCD)
Figure 5:
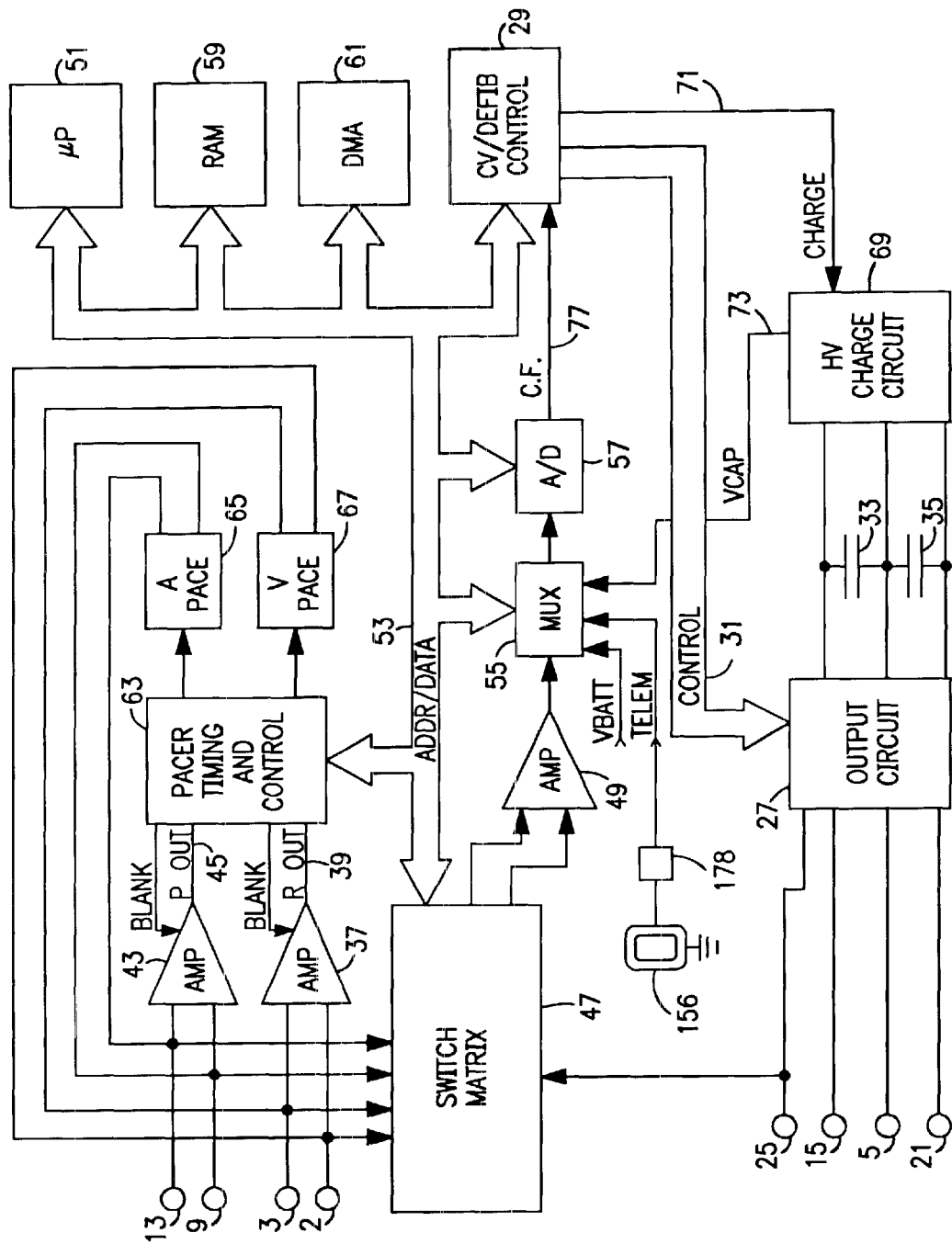
FIG. 5 is a functional block diagram of the IMD of FIG. 4.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative. lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

The implantable PCD is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other than those shown in FIG. 4 may be practiced in conjunction with the present invention, such as those shown in U.S. Pat. No. 5,690,686 to Min et al.

FIG. 5 is a functional schematic diagram of one embodiment of an implantable PCD of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

The PCD is provided with an electrode system. If the electrode configuration of FIG. 4 is employed, the electrode configuration correspondence may be as follows. Electrode 25 in FIG. 5 includes the uninsulated portion of the housing of the PCD. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, to Keimel et al.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selection may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known in the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacertiming/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known in the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann et al., U.S. Pat. No. 4,880,005 issued to Pless et al. and U.S. Pat. No. 4,830,006 issued to Haluska et al. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547.

In the event an atrial or ventricular tachyarrhythmia is detected and an anti-tachyarrhythmia pacing regimen is desired, appropriate timinig intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al. and U.S. Pat. No. 4,587,970, issued to Holley et al., may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and, in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al. However, any known cardioversion or defibrillation pulse control circuitry is believed to be usable in conjunction with various embodiments of the present invention. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. Examples of output circuitry for delivery of biphasic pulse regimens to multiple electrode systems may be found in U.S. Pat. No. 4,953,551 to Mehra et al. and in U.S. Pat. No. 4,727,877 to Kallock.

Like the pacemaker IMD illustrated in FIG. 3, the PCD of FIG. 5 also includes RF transmitter and receiver telemetry unit 178 coupled to antenna 156 to permit communication therewith.

An example of circuitry which may be used to control delivery of monophasic pulses is disclosed in U.S. Pat. No. 5,163,427 to Keimel. Output control circuitry similar to that disclosed in the above cited patent issued to Mehra et al. or U.S. Pat. No. 4,800,883 to Winstrom, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennett et al. The present invention is believed to find wide application to any form of implantable electrical device.

Various embodiments of IMD 10 are described above. Accordingly, attention is now directed to telemetry control systems and methods for their use with IMDs.

Figure 6:
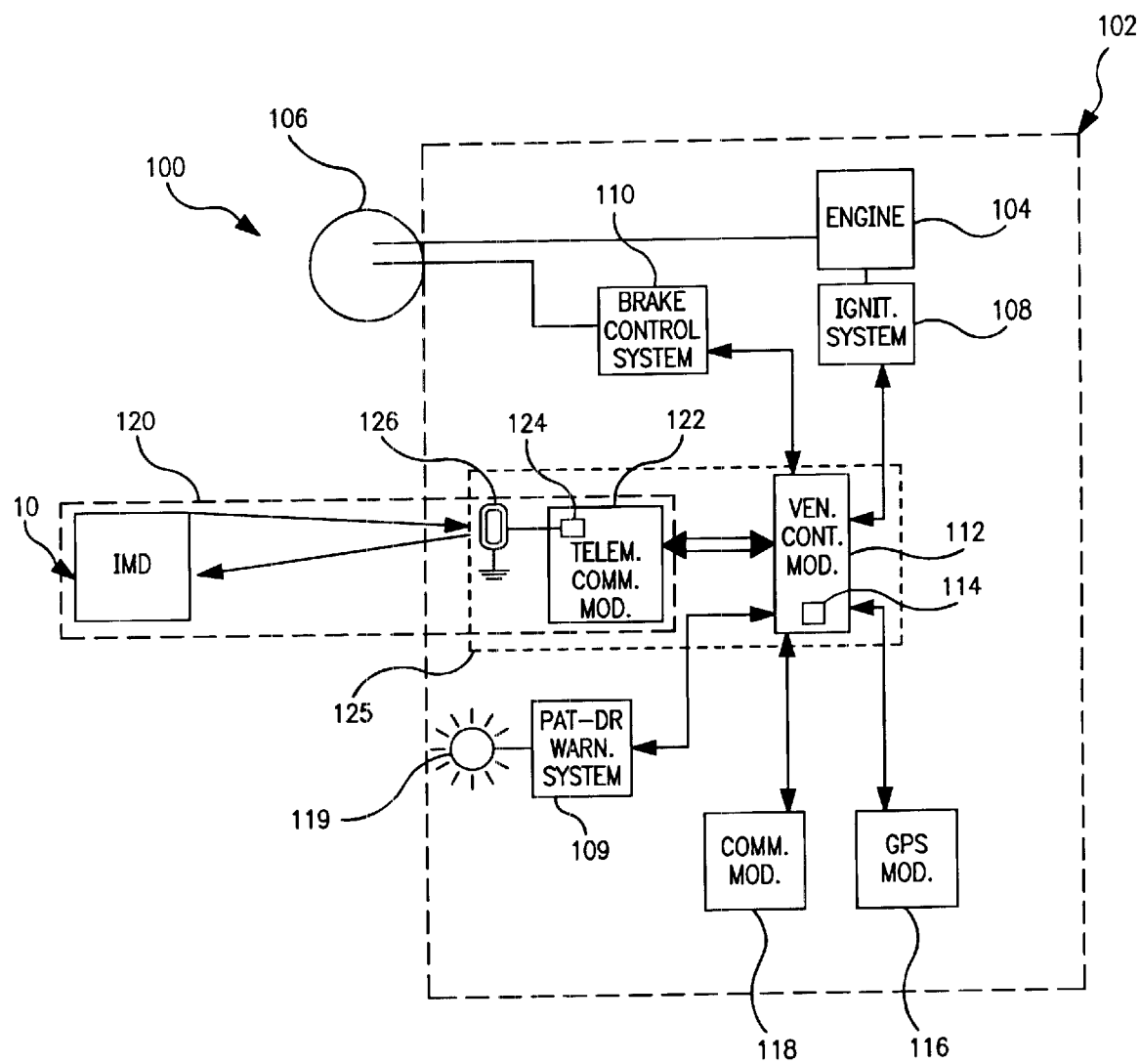
FIG. 6 is a block diagram of an IMD telemetry control system in accordance with one embodiment of the present invention.

FIG. 6 diagrammatically illustrates IMD telemetry control system 100 in accordance with one embodiment of the invention. For purposes of discussion, telemetry control system 100 will be shown and described primarily with reference to the PCD illustrated in FIGS. 4 and 5 and 10 discussed herein above. One example of a PCD in accordance with the present invention is the model "Jewel AF" manufactured by Medtronic, Inc. of Minneapolis, Minn. However, control system 100 may be adapted to operate with most any cardiac and non-cardiac IMD as described herein or otherwise recognized in the art.

The telemetry control system of the present invention is further described herein with particular reference to automobiles. However, this too, is not to be considered limiting. In fact, control system 100 may be adapted to function with most any IMD 10 and most any vehicle or machine in which vehicle/machine status would be beneficial to the operation of the IMD. For example, control system 100 could be adapted to work with construction equipment, agricultural equipment, manufacturing and production machinery, etc. Nonetheless, the present invention is particularly advantageous to automobiles and the remainder of this discussion will focus accordingly.

FIG. 6 illustrates control system 100 including IMD 10 and vehicle 102. Vehicle 102 comprises prime mover, e.g., engine 104, coupled to one or more ground-engaging traction wheels 106 (only one shown) via a transmission (not shown). The vehicle also includes several subsystems such as ignition system 108 for controlling the status, e.g., engine on/off, and speed, e.g., throttle setting, of engine 104. The vehicle further includes brake control system 110. Brake control system 110 controls the braking of traction wheels 106 and may optionally include an anti-lock brake system ("ABS") and/or traction control capability. Patient-driver warning system 109 with warning/alert indicator 119 is also illustrated and further described below. Modern vehicles include a vast array of other subsystems that, while advantageous to vehicle operation, are not particularly pertinent to an understanding of the present invention and are thus not described herein. However, it is understood that any vehicle subsystem may be controlled according to the present invention.

Brake control system 110, warning system 109 and ignition system 108 communicate with vehicle control module 112 as illustrated in FIG. 6. In one embodiment, control module 112 is what is commonly referred to as the vehicle microcomputer. As embodied in the present invention, control module 112 can interrogate or poll the status of the various vehicle subsystems. In other embodiments, module 112 may also transmit command outputs to the various subsystems, e.g., brake control and ignition. That is, control module 112 can manipulate the vehicle from a first operational state, e.g., moving, to a second operational state, e.g., stopped. For example, control module 112 may monitor engine speed and, upon the occurrence of a predetermined condition, issue a command to ignition system 108 to either slow the engine or shut it down.

To process information, control module 112 includes central processing unit (CPU) 114 also diagrammatically illustrated in FIG. 6. Processor 114 and its control circuitry are capable of executing a pre-programmed set of algorithms based on inputs from various sensors and the various subsystems and outputting status and/or control signals in response thereto. For instance, CPU 114 may monitor wheel speed and compare it to vehicle and/or engine speed. When a discrepancy exists, CPU 114 may engage brake control system 110 or adjust engine throttle to correct the detected discrepancy.

Vehicle control module 112 may optionally communicate with global positioning system (GPS) module 116 and/or communication module 118, e.g., cellular telephone, located within vehicle 102. When so configured, processor 114 may initiate contact via communication module 118 and relay vehicle position as provided by GPS module 116.

To provide feedback to the patient-driver concerning the status of vehicle 102, patient-driver warning system 109 may include one or more alert or alarm indicators 119. FIG. 6 illustrates alert indicator as a visual, e.g., dashboard-mounted, warning light 119. However, other embodiments may include an audible, e.g., voice, alarm or, more preferably, a combined audible and visual alert indicator.

Control system 100 further includes telemetry communication apparatus 120. Apparatus 120 includes IMD 10, located within the patient-driver, and telemetry communication module (TCM) 122.

The purpose of TCM 122 is to receive telemetry data from and, in some embodiments, transmit vehicle status data to IMD 10. This may be accomplished via low power, encoded radio frequency (RF) transmissions or any other suitable telemetry technique. For example, in one embodiment, an RF transmitter and receiver telemetry unit 178 (see FIG. 5) located within IMD 10 transmits data to a receiver of TCM 122 and receives data through RF antenna 156 (see also FIG. 5) from a transmitter of TCM 122. "Telemetry," as used herein, may refer to both unidirectional and/or bidirectional, i.e., both signal transmission and reception, telemetry.

TCM 122 uses telemetry transmitter and receiver unit 124 (see FIG. 6), i.e., a unit compatible with IMD transmitter and receiver telemetry unit 178 (see FIG. 5), coupled to antenna 126 for communication between IMD 10 and vehicle control module 112. Antenna 126 is preferably located close to the torso of the patient-driver to ensure adequate reception and transmission of the various telemetry signals. In one embodiment, antenna 126 is located in the steering column, preferably in the steering wheel of vehicle 102. In another embodiment, antenna 126 is located in the driver's seat. However, the exact location of antenna 126 may vary. Its location is ideally selected to ensure adequate signal transmission to and reception from antenna 156 (see FIG. 5) of IMD 10.

TCM 122, like other vehicle subsystems, is electrically coupled to CPU 114 of vehicle control module 112 as indicated in FIG. 6. While illustrated in FIG. 6 as a separate component, TCM 122 may alternatively be incorporated into vehicle control module 112 as generally represented by dashed lines 125. Further, all communication between portions of the system, e.g., between TCM 122 and vehicle control module 112, may be performed by wireless or, alternatively, physical electrical coupling.

Operation

The operation of telemetry control system 100 will be described with particular reference to FIGS. 7–9. These figures illustrate the operation of control system 100 upon detection of various cardiac events. Each figure is arranged in columns to more clearly indicate where particular activity occurs. For instance, the leftmost column describes activity within IMD10. Moving to the right, the next column describes activity within CPU 114 of control module 112; followed by activity within ignition system 108; and lastly, activity within the brake control system 110. For simplicity, activity in warning system 109, communication module 118 and GPS module 116 are illustrated in the figures as CPU events.

The illustrations and following description explain the invention as it may be embodied in a cardiac IMD. However, other IMDs that sense most any medical event, i.e., any physiological event or change in the state of the body, are also envisioned within the scope of the invention.

While the embodiment of FIG. 6 illustrates particular subsystems, those of skill in the art will recognize that most any vehicle subsystem could be adapted to operated with system 100 without departing from the scope of the invention. It is further noted that the algorithms described in FIGS. 7–9 are exemplary only. Accordingly, numerous other actions may be programmed to take place upon the detection of most any cardiac event.

Figure 7:
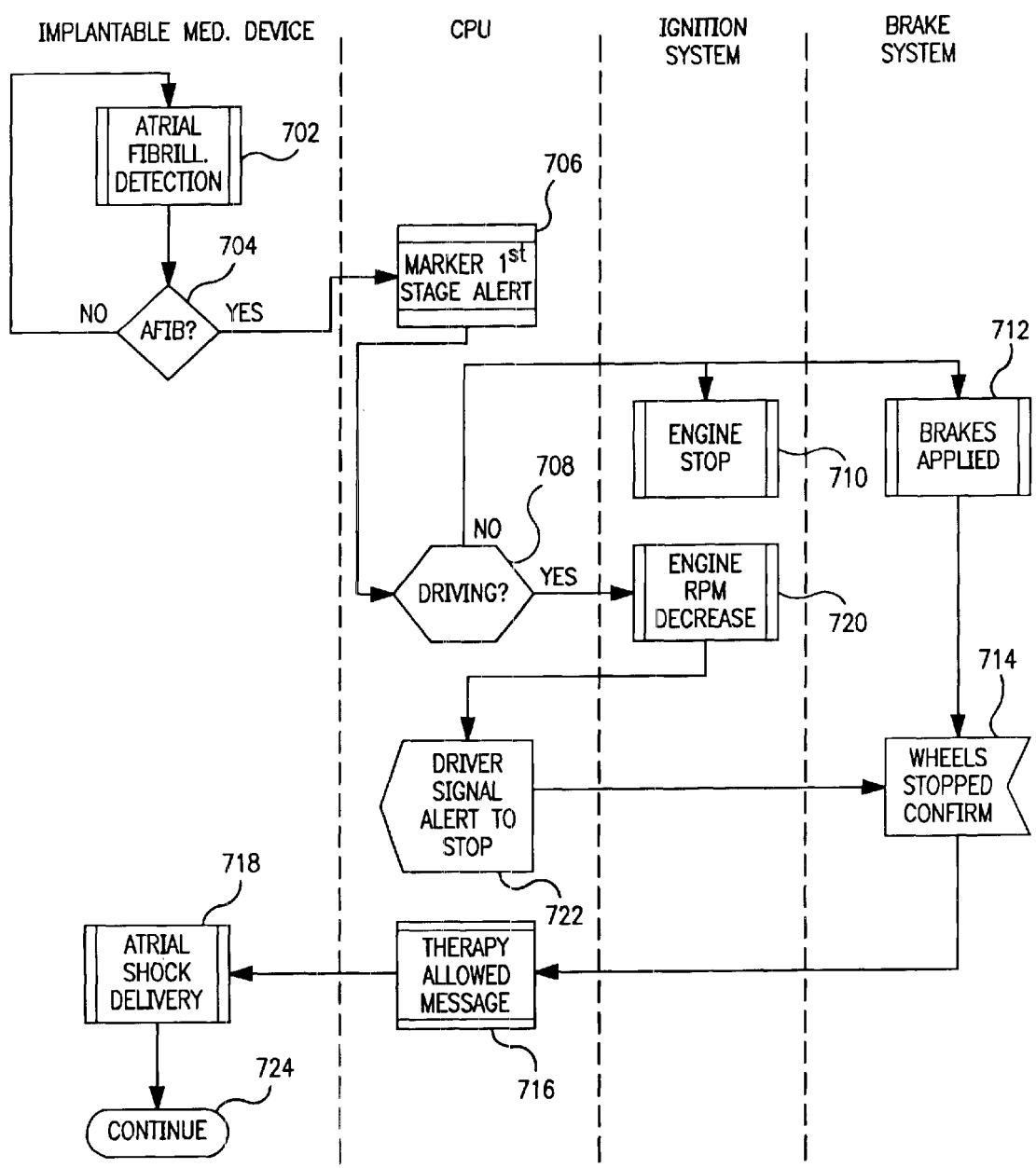
FIG. 7 is a block diagram illustrating the operation of the telemetry control system of FIG. 6 in accordance with one embodiment of the invention.

FIG. 7 illustrates operation of telemetry control system 100 in the event of atrial fibrillation detection within the patient-driver. IMD 10 continuously polls sensing electrode, e.g., electrodes 3 and 9 as shown in FIG. 5, at 702 and 704. When the sensing circuitry of IMD 10 detects the occurrence of a medical event, e.g., atrial fibrillation, at 704, an event signal corresponding to the medical event is transmitted from RF transmitter and receiver 178 (see FIG. 5) via antenna 156 to antenna 126 of receiver and transmitter 124 of TCM 122 (See FIG. 6). CPU 114 (see also FIG. 6) may then mark or initiate a first stage alert, e.g., activation of indicator 119 (see FIG. 6), as indicated at 706. Indicator 119 informs the patient-driver that atrial fibrillation has been detected and that therapy will subsequently follow.

Although atrial fibrillation therapy is not normally incapacitating, the potential for distracting or upsetting the patient-driver remains. Accordingly, CPU 114 initiates a control algorithm that first determines if the vehicle is moving at 708. If not, CPU 114 deactivates ignition system 108 (see FIG. 6) as shown at 710. Further, CPU 114 locks brake system 110 (see also FIG. 6) as shown at 712 and confirms that the vehicle wheels are locked at 714. At this point, CPU 114 generates a "therapy allowed" status signal at 716 and transmits the status signal from receiver and transmitter 124 of TCM 122 (see FIG. 6) via antenna 126 to RF transmitter and receiver 178 (see FIG. 5) of IMD 10 via antenna 156. The status signal indicates that the vehicle has reached a particular operational status, e.g., stopped, suitable for therapy delivery. Once IMD 10 receives the status signal, microcomputer circuit 51 (see also FIG. 5) commands IMD 10 to deliver atrial shock therapy via output circuit 27 (see FIG. 5) as indicates at 718.

In the event that CPU 114 determines the vehicle is moving at 708, it initiates a different algorithm. In one embodiment, CPU 114 first commands ignition system 108 to decrease engine speed as indicated at 720. Thereafter or simultaneous with the command to decrease engine speed, CPU 114 may also initiate a second alert indicator to the patient-driver to stop the vehicle as shown at 722. The second alert indicator may also be a visual or audible warning incorporated into or separate from indicator 119. Once wheel stop is confirmed at 714, the CPU delivers the therapy allowed message at 716 and IMD 10 proceeds to deliver therapy at 718.

Upon completion of therapy delivery, telemetry control system 100 resets and returns to detection mode at 724. Various algorithms may then initiate to ensure the safe return of control of the vehicle to the patient-driver. For example, the system may reset and return control to the patient-driver immediately. Alternatively, the system may prevent operation of the vehicle for a specific period of time. In another embodiment, the system may require the patient-driver to initiate some sequence of actions, e.g., input a security code, before control is returned. In still another embodiment, the vehicle may require authorized service before operation. The exact method used to return control of the vehicle to the patient-driver may be selected based on the particular medical event detected.

Figure 8:
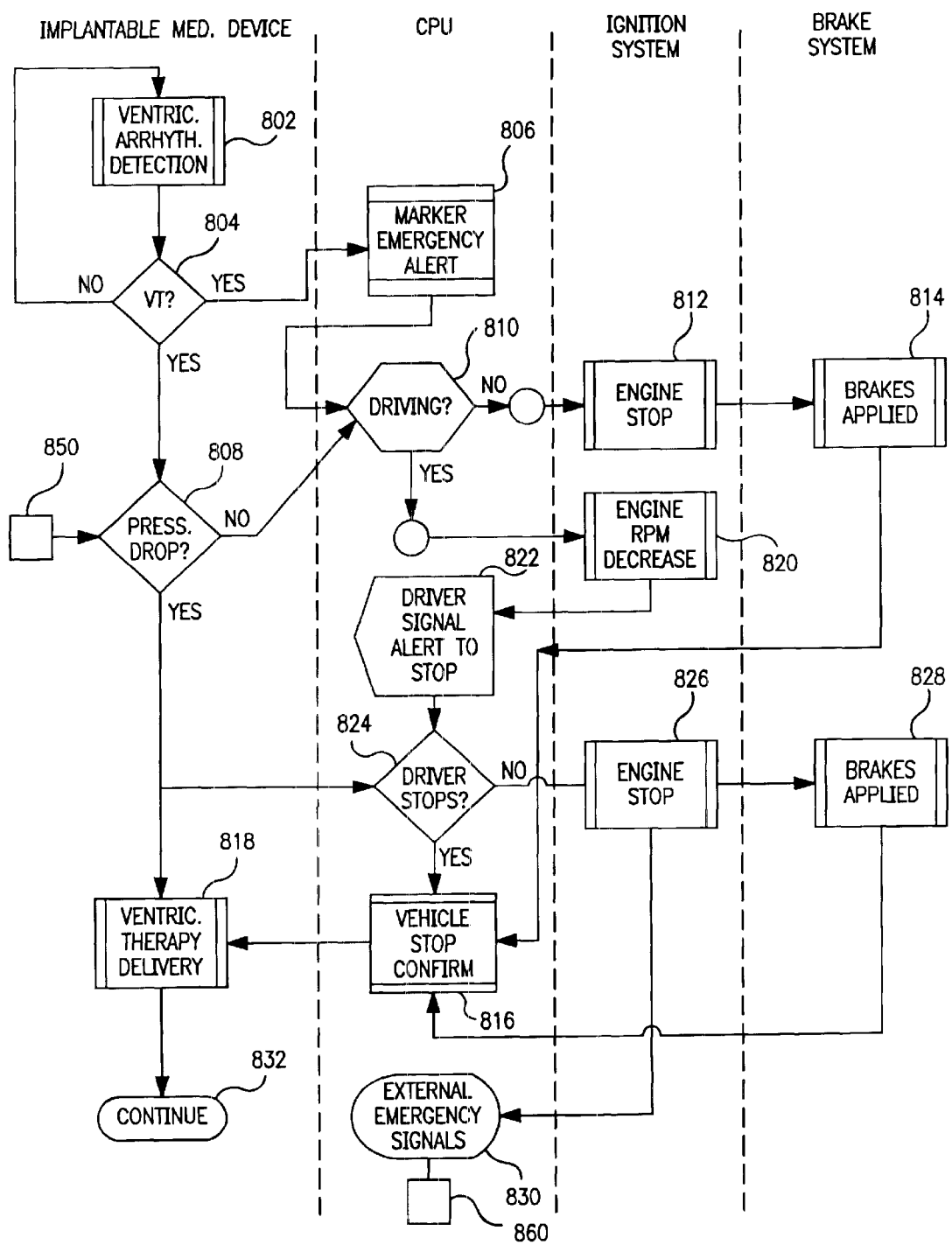
FIG. 8 is a block diagram illustrating the operation of the telemetry control system of FIG. 6 in accordance with another embodiment of the invention.

FIG. 8 is a block diagram similar to that of FIG. 7 but describing the operation of telemetry control system 100 in response to detection of a ventricular tachycardia (VT). In this instance, IMD 10 may additionally comprise hemodynamic sensor 850 for detecting a hemodynamic parameter such as blood pressure or intracardial flow. The sensor, while not specifically shown in FIG. 5, is coupled to microprocessor circuit 51. Sensor 850 permits IMD 10 to discriminate between hemodynamically stable versus unstable arrhythmia.

IMD 10 continuously polls sensing electrodes, e.g., electrodes 3 and 9 as shown in FIG. 5, at 802 and 804. When the sensing circuitry of IMD 10 detects the occurrence of VT at 804, an event signal is transmitted from RF transmitter and receiver 178 (see FIG. 5) to receiver and transmitter 124 of TCM 122 (See FIG. 6). CPU 114 (see also FIG. 6) then initiates an emergency alert as indicated at 806. The alert, e.g., indicator 119 (see FIG. 6), informs the patient-driver that a VT has been detected and therapy will subsequently follow.

After or simultaneously with notifying the patient-driver of the VT, CPU 114 determines whether or not the vehicle is moving at 810. If the vehicle is not moving, CPU 114 commands ignition system 108 (see FIG. 6) to stop at 812 and brake system 110 to lock the wheels at 814. Once wheel lock is confirmed by CPU 114 at 816, the CPU generates a status signal and transmits it via receiver and transmitter 124 of TCM 122 (See FIG. 6) to RF transmitter and receiver 178 of IMD 10 (see FIG. 5). Upon receipt of the status signal, IMD 10 delivers VT therapy as indicated at 818.

Alternatively, if CPU 114 determines the vehicle is moving at 810, it commands ignition system 108 to reduce engine speed at 820 and provides a second alert indicator to the patient-driver to stop the vehicle as indicated at 822. If CPU 114 determines the patient-driver has stopped at 824, control is returned to 816 as described above. If, however, CPU 114 determines that the patient-driver is not stopping the vehicle at 824, it commands ignition system 108 to stop at 826 and brake system 110 to brake the wheels at 828. Once ignition system 108 reports that the engine is stopped, or, in conjunction with stopping, CPU 114 may optionally activate external emergency signals 860, e.g., flashing exterior lights, at 830 to warn other vehicles. Upon confirmation that the wheels are stopped and locked at 816, CPU 114 generates a status signal and transmits it via receiver and transmitter 124 of TCM 122 (see FIG. 6) to RF transmitter and receiver 178 of IMD 10 (see FIG. 5). Upon receipt of the status signal, IMD 10 delivers VT therapy as indicated at 818.

Because hemodynamically unstable VT requires immediate therapy, IMD 10 interrogates hemodynamic sensor 850 immediately and optionally, continuously, after VT detection. If IMD 10 detects a change, e.g., a drop in blood pressure at 808, it immediately delivers VT therapy at 818 regardless of vehicle status. Simultaneous with the delivery of therapy, CPU 114 may command the vehicle ignition and brake systems to bring the vehicle to a stop as described above without reliance on input from the potentially incapacitated patient-driver. However, if the VT is determined to be hemodynamically stable at 808, e.g., no significant pressure drop, VT therapy is delayed and system control is returned to CPU 114 at 810.

After VT therapy, telemetry control system 100 returns to detection mode as indicated at 832. Control of the vehicle may be to returned in accordance with the methods described above with respect to FIG. 7.

Figure 9:
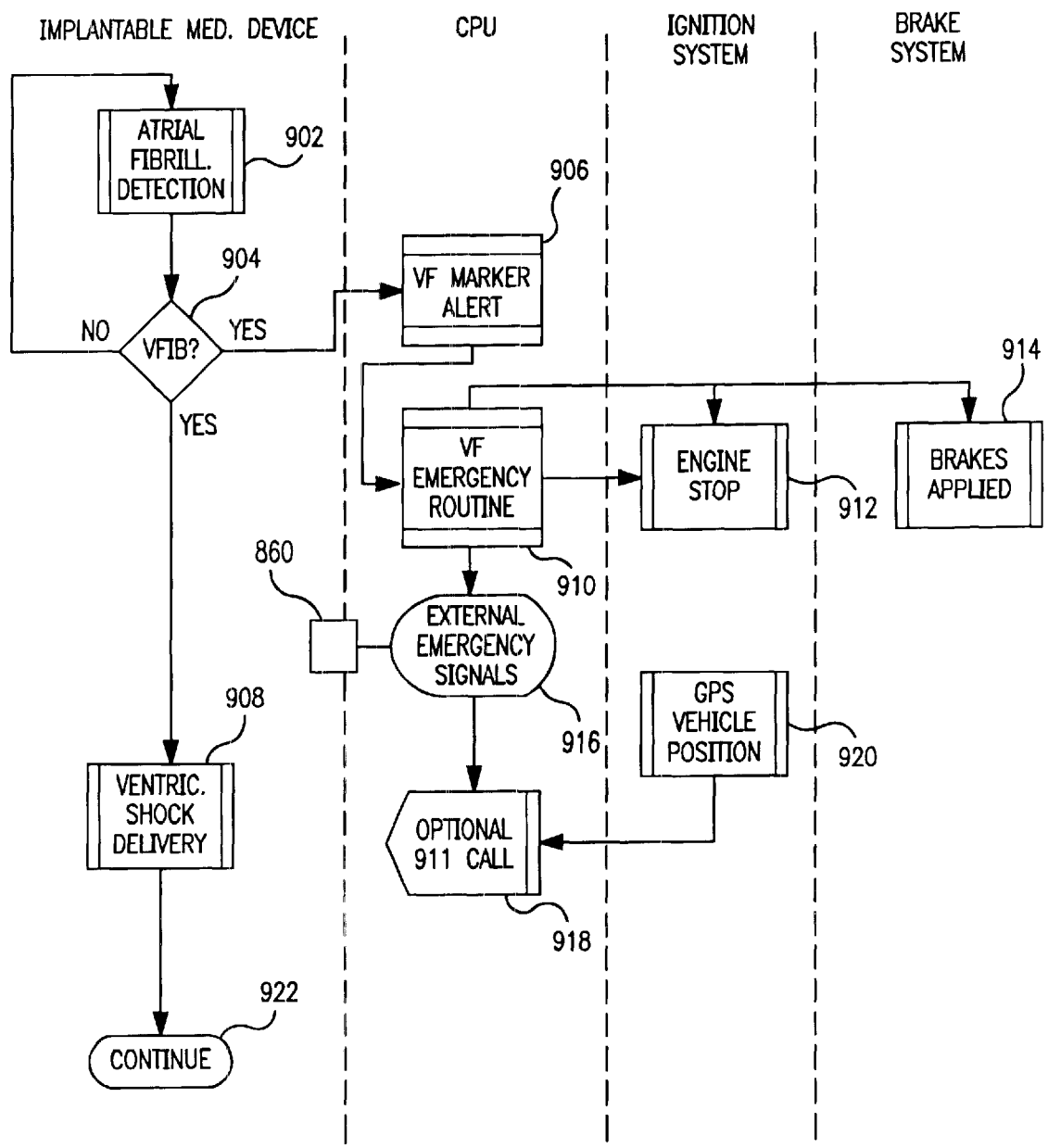
FIG. 9 is a block diagram illustrating the operation of the telemetry control system of FIG. 6 in accordance with still another embodiment of the invention.

FIG. 9 illustrates operation of telemetry control system 100 in response to a detected ventricular fibrillation (VF) in the patient-driver. Once again, IMD 10 continuously polls a sensing electrode, e.g., electrodes 3 and 9 as shown in FIG. 5, at 902 and 904. When IMD 10 detects the occurrence of VF at 904, an event signal is transmitted from RF transmitter and receiver 178 (see FIG. 5) to receiver and transmitter 124 of TCM 122 (See FIG. 6). CPU 114 (see also FIG. 6) then initiates a VF alert by activating indicator 119 (FIG. 6) as indicated at 906. Indicator 119 informs the patient-driver that VF has been detected and therapy will subsequently follow.

Because VF requires immediate therapy, the algorithm for VF detection initiates IMD capacitor charge and vehicle stopping simultaneously. That is, VF shock therapy is delivered immediately to the patient-driver as indicated at 908. After therapy delivery, IMD 10 returns to detection mode (in accordance with the methods described above with respect to FIG. 7) as indicated at 922.

In parallel with therapy delivery is a VF emergency routine indicated at 910. The VF emergency routine is executed by CPU 114 and, in one embodiment, commands ignition system 108 to stop the engine at 912 and further commands the brake system to slow the vehicle to full stop at 914. CPU 114 may also activate external emergency signals 860 at 916 to warn other vehicles.

Due to the seriousness of the VF event and its accompanying therapy, CPU 114 may optionally initiate a rescue call utilizing onboard communication module 118 (see FIG. 6) as indicated at 918. To expedite the 911 call, an emergency broadcast may automatically provide information to the rescue operator communicating the severity of the patient-driver's condition. By utilizing GPS module 116 (see FIG. 6) as indicated at 920, the exact location of the vehicle can also be relayed to the rescue operator, further accelerating the arrival of rescue personnel to the scene.

While shown only in FIG. 9, the utilization of communication module 118 and GPS module 116 can be incorporated into any of the detection algorithms such as VT detection as illustrated in FIG. 8 and AF detection as illustrated in FIG. 7. In fact, the actual embodiments illustrated in the figures and described above are not intended to be limiting but rather exemplary of particular telemetry control systems envisioned to provide adequate vehicle control and feedback in response to a cardiac event. Other vehicle control parameters and features, e.g., horn, interior/exterior lights, and door locks, etc., may also communicate with vehicle control module 112 for utilization with telemetry control system 100.

Likewise, the algorithms and the particular sequence of events within the algorithms may be altered to better suit the particular cardiac event or even customized to the needs of the particular cardiac patient-driver. Further, because the illustrated embodiments are exemplary only, events described and illustrated herein as occurring sequentially may also occur simultaneously without departing from the scope of the invention. Stii; further, the systems described herein are microprocessor-based. However, other systems may be implemented using non-processor based components and logic techniques.

Telemetry control systems in accordance with the present invention may be used in conjunction with other IMDs, e.g., neurologic implants, nerve stimulators, muscle stimulators, or, alternatively, external medical devices, e.g., respiratory monitors, that may incorporate the circuits necessary for communication and operation as described herein. In addition, as vehicle computers become more sophisticated and standardized, telemetry control systems in accordance with the present invention may be adapted to function not only with the subsystems described herein, but also with other subsystems now known and those not yet commercially available. For instance, the present invention may be adapted to operate in conjunction with a collision avoidance system or with other vehicle proximity sensors to better coordinate automated stopping of the vehicle.

Telemetry control systems in accordance with the present invention may also be used to communicate other patient-driver/vehicle information. For instance, the system could detect when the patient-driver is operating the vehicle and activate various vehicle limitations/warnings such as maximum speed limitations and restrictions on nighttime driving.

Advantageously, telemetry systems in accordance with the present invention permit patients having IMD implants to continue operating a motor vehicle after implantation. In the event of a minor medical event, the patient-driver is given adequate warning to stop the vehicle prior to therapy delivery. In the event of an incapacitating medical event, the telemetry control system may activate various controls to assist or even assume control of the vehicle, bringing it to a stop without reliance on patient-driver input. In other embodiments, the telemetry control system may automatically summon emergency assistance upon the occurrence of a medical event.

The complete disclosure of the patents, patent documents, and publications cited in the Background, Detailed Description of the Embodiments and elsewhere herein are incorporated by reference in their entirety as if each were individually incorporated.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to the use of IMDs for cardiac therapy but may, as mentioned above, be used with most any medical device, implanted or external. Further, the present invention can be modified to communicate with most any subsystem of the automobile, permitting numerous permutations within the scope of the invention. The present invention further includes within its scope methods of making and using the telemetry systems described herein above.

What is claimed is:

1. An implantable medical device telemetry apparatus for use with a vehicle, comprising:

an implantable medical device operable to determine occurrence of at least one medical event, the implantable medical device having a transmitter capable of transmitting at least one event signal representative of the medical event; and a vehicle control module associated with the vehicle, the vehicle control module also associated with a receiver for receiving the at least one event signal, wherein the vehicle control module is adapted to manipulate at least one vehicle subsystem in response to the at least one event signal.

2. The apparatus of claim 1, wherein the implantable medical device is capable of delivering therapy to a body.

3. The apparatus of claim 2, wherein the at least one event signal corresponds to a detected need to deliver therapy.

4. The apparatus of claim 1, wherein the implantable medical device is a cardiac pacing device.

5. The apparatus of claim 1, wherein the implantable medical device is at least one of a pacemaker, cardioverter, or defibrillator.

6. The apparatus of claim 1, wherein the at least one vehicle subsystem comprises a patient-driver warning system controllable by the vehicle control module.

7. The apparatus of claim 1, wherein the at least one vehicle subsystem comprises an ignition system controllable by the vehicle control module.

8. The apparatus of claim 1, wherein the at least one vehicle subsystem comprises a braking system controllable by the vehicle control module.

9. The apparatus of claim 1, wherein the implantable medical device further comprises a device receiver and the vehicle control module is further associated with a telemetry transmitter, wherein the telemetry transmitter is operable to transmit a status signal indicative of vehicle status for receipt by the device receiver.

10. An implantable medical device for implantation within a body, the device comprising:

a housing;

sensor circuitry coupled to the housing and operable to determine the occurrence of a medical event;

therapy delivery circuitry within the housing operable to deliver therapy to the body;

control circuitry within the housing operable to control delivery of therapy by the therapy delivery circuitry; and a transmitter associated with the housing operable to provide an event signal to a vehicle control module located outside the body when the sensor circuitry determines the occurrence of the medical event;

wherein the control circuitry is adapted to coordinate delivery of the therapy with the vehicle control module upon the occurrence of the medical event.

11. The device of claim 10, further comprising a receiver associated with the housing, the receiver operable to receive a status signal from the vehicle control module for use in coordinating the delivery of the therapy.

12. The device of claim 11, wherein the control circuitry is adapted to coordinate delivery of the therapy with the receipt of the status signal, the status signal indicative of a state of a vehicle.

13. The device of claim 10, wherein the control circuitry comprises a microprocessor within the housing, the microprocessor electrically coupled to the sensor circuitry, therapy delivery circuitry, control circuitry and the transmitter.

14. The device of claim 10, wherein the therapy delivery circuitry is operable to provide cardiac therapy.

15. The device of claim 10, wherein the implantable medical device is at least one of a pacemaker, cardioverter, and defibrillator.

16. The device of claim 10, wherein the sensor circuitry detects irregular cardiac activity.

17. The device of claim 10, wherein the sensor circuitry detects ventricular arrhythmia.

18. The device of claim 10, wherein the sensor circuitry detects ventricular fibrillation.

19. The device of claim 10, wherein the sensor circuitry detects atrial fibrillation.

20. A method of delivering therapy to a patient during operation of a vehicle, the method comprising:

providing an implantable medical device within a body, the implantable medical device having a device transmitter;

providing a vehicle, comprising:
a vehicle control module; and
a telemetry communication module associated with the vehicle control module, the telemetry communication module having a telemetry receiver capable of receiving one or more event signals from the device transmitter and providing the one or more event signals to the vehicle control module;

detecting a medical event with the implantable medical device and generating an event signal in response thereto;

transmitting the event signal from the device transmitter to the telemetry receiver; and manipulating the status of one or more vehicle subsystems with the vehicle control module in response to the event signal.

21. The method of claim 20, wherein manipulating the status of one of more vehicle subsystems comprises activating an alert indicator.

22. The method of claim 21, wherein the alert indicator includes at least one of a visual indicator or an audible indicator.

23. The method of claim 20, wherein manipulating the status of one of more vehicle subsystems comprises deactivating a vehicle ignition system.

24. The method of claim 20, wherein manipulating the status of one of more vehicle subsystems comprises reducing the speed of the vehicle.

25. The method of claim 20, wherein manipulating the status of one of more vehicle subsystems comprises activating a brake system to stop or slow the vehicle.

26. The method of claim 20, wherein manipulating the status of one of more vehicle subsystems comprises activating one or more external emergency signals on the vehicle.

27. The method of claim 20, wherein manipulating the status of one of more vehicle subsystems comprises activating a communication module to notify remote emergency personnel of the medical event.

28. The method of claim 27, further comprising transmitting a position signal with the communication module, the position signal indicative of vehicle location.

29. The method of claim 20, further comprising:
polling the status of the one or more vehicle subsystems with the vehicle control module and generating a status signal based thereon; and
transmitting the status signal from a transmitter in the telemetry communication module to a receiver in the implantable medical device.

30. The method of claim 29, further comprising delivering a therapy to the body with the implantable medical device after receipt of the status signal.

31. The method of claim 29, further comprising delivering a therapy to the body with the implantable medical device before receipt of the status signal.

32. The method of claim 20, wherein manipulating the status of one or more vehicle subsystems comprises generating a command output with the vehicle control module, the command output operable to slow or stop the vehicle.

33. The method of claim 32, wherein the command output is used to control an ignition system to slow or stop a vehicle engine.

34. The method of claim 32, wherein the command output is used to control a brake system to slow or stop the vehicle.

35. A vehicle control module for use with an implantable medical device, the vehicle control module comprising:
a telemetry communication module;
is control circuitry coupled to the telemetry communication module, the telemetry communication module adapted to receive one or more event signals from the implantable medical device and provide the one or more event signals to the control circuitry; and
a command output coupled to the control circuitry, wherein the command output is adapted to manipulate one or more vehicle subsystems in response to the one or more event signals.

36. The control module of claim 35, wherein the one or more vehicle subsystems comprises a patient-driver warning system controllable by the vehicle control module.

37. The control module of claim 35, wherein the vehicle subsystem comprises a brake system controllable by the vehicle control module.

38. The control module of claim 35, wherein the vehicle subsystem comprises an ignition system controllable by the vehicle control module.

39. The control module of claim 38, wherein the ignition system is adapted to manipulate engine speed.

40. The control module of claim 38, wherein the ignition system is adapted to deactivate the engine.

41. The control module of claim 35, wherein the telemetry communication module is further adapted to transmit a status signal to the implantable medical device.

42. A vehicle, comprising:
a prime mover;
two or more ground engaging traction wheels wherein at least one wheel is coupled to the prime mover; and
a vehicle control module, comprising:
a telemetry communication module having a receiver for receiving event signals from an implantable medical device representative of an occurrence of a medical event; and
control circuitry to receive the event signals and provide, in response to the event signals, a command output, wherein the command output is adapted to manipulate one or more vehicle subsystems in response to the event signals.

43. The vehicle of claim 42, wherein the one or more vehicle subsystems is a brake system operable to stop one or more traction wheels.

44. The vehicle of claim 42, wherein the one or more vehicle subsystems is an ignition system operable to disable the prime mover.

45. The vehicle of claim 42, wherein the one or more vehicle subsystems is an ignition system operable to slow the speed of the prime mover.

46. The vehicle of claim 42, wherein the one or more vehicle subsystems is a warning system operable to notify a patient-driver of the event signal.

47. The vehicle of claim 42, wherein the telemetry communication to module further comprises a transmitter adapted to transmit a status signal representative of a state of the vehicle to the implantable medical device.

48. A method for providing therapy to a patient-driver of a vehicle, the method comprising:
providing an implantable medical device in the patient-driver, the implantable medical device capable of sensing a medical event and delivering a therapy in response to the medical event, wherein the implantable medical device further comprises a device transmitter for transmitting an event signal representative of the medical event;
providing a vehicle control module coupled to the vehicle for controlling one or more vehicle subsystems, the vehicle control module associated with a telemetry communication module having a telemetry receiver for receiving the event signal from the implantable medical device;
sensing a medical event with the implantable medical device;
generating an event signal with the implantable medical device; and
transmitting the event signal with the device transmitter to the telemetry receiver.

49. The method of claim 48, further comprising interrogating the vehicle with the vehicle control module to determine the vehicle status.

50. The method of claim 48, further comprising delivering therapy to the patient-driver with the implantable medical device.

51. The method of claim 48, further comprising manipulating the vehicle between a first operational state and a second operational state in response to the event signal.

52. The method of claim 51, further comprising delivering therapy to the patient-driver with the implantable medical device after manipulation of the vehicle to the second operational state.

53. The method of claim 49, further comprising:
generating-a status signal with the vehicle control module, the status signal corresponding to the vehicle status;
transmitting the status signal from a telemetry transmitter of the telemetry control module to a device receiver of the implantable medical device; and
delivering therapy to the patient-driver with the implantable medical device as a function of the status signal.

54. The method of claim 53, wherein generating the status signal occurs after the vehicle control module determines that the vehicle is stopped.

55. The method of claim 51, further comprising:
generating a status signal with the vehicle control module, the status signal corresponding to the second operational state;
transmitting the status signal from a telemetry transmitter to a device receiver of the implantable medical device; and
delivering therapy to the patient-driver with the implantable medical device.

56. The method of claim 55, wherein generating the status signal occurs after the vehicle control module determines that the vehicle is stopped.

57. The method of claim 55, wherein delivering therapy to the patient-driver occurs after receipt of the status signal by the device receiver.

58. The method of claim 55, wherein delivering therapy to the patient-driver occurs before receipt of the status signal by the device receiver.

59. The method of claim 51, wherein manipulating the vehicle between the first operational state and the second operational state comprises manipulating an ignition system to stop or slow the vehicle.

60. The method of claim 51, wherein manipulating the vehicle between the first operational state and the second operational state comprises manipulating a brake system to stop or slow the vehicle.

61. The method of claim 51, wherein manipulating the vehicle between the first operational state and the second operational state comprises activating a warning indicator to alert the patient-driver of the medical event.

62. The method of claim 51, wherein manipulating the vehicle between the first operational state and the second operational state comprises activating external warning signals on the vehicle.

63. The method of claim 48, further comprising activating a communication module to notify emergency personnel of the medical event.

64. The method of claim 63, further comprising generating a location signal of the vehicle and transmitting the location signal via the communication module.

65. The method of claim 48, wherein the medical event is an atrial fibrillation.

66. The method of claim 48, wherein the medical event is a ventricular tachycardia.

67. The method of claim 48, wherein the medical event is a ventricular fibrillation.

68. The method of claim 66, further comprising sensing a hemodynamic parameter.

69. The method of claim 68, further comprising delivering cardiac therapy upon detection of the hemodynamic parameter.

70. The method of claim 68, wherein the hemodynamic parameter is blood pressure.

71. The method of claim 68, wherein the hemodynamic parameter is intracardial flow.

* * * * *